United States Patent
Kim (10) Patent No.: US 9,070,177 B2
(45) Date of Patent: Jun. 30, 2015

(54) AUTOMATIC MEDICINE WAREHOUSING AND RELEASING MANAGEMENT SYSTEM AND METHOD OF AUTOMATICALLY WAREHOUSING AND RELEASING MEDICINES THEREOF

(75) Inventor: Jun-Ho Kim, Daegu (KR)

(73) Assignee: JVM CO., LTD., Daegu (KR)

( * ) Notice: Subject to any disclaimer, the term of this patent is extended or adjusted under 35 U.S.C. 154(b) by 0 days.

(21) Appl. No.: 13/979,959

(22) PCT Filed: Feb. 20, 2012

(86) PCT No.: PCT/KR2012/001240
§ 371 (c)(1),
(2), (4) Date: Jul. 16, 2013

(87) PCT Pub. No.: WO2012/112010
PCT Pub. Date: Aug. 23, 2012

(65) Prior Publication Data
US 2013/0325168 A1 Dec. 5, 2013

(30) Foreign Application Priority Data
Feb. 18, 2011 (KR) .................... 10-2011-0014714

(51) Int. Cl.
*G06F 7/00* (2006.01)
*G06Q 50/28* (2012.01)
*G06Q 10/08* (2012.01)
*G06Q 50/22* (2012.01)

(52) U.S. Cl.
CPC ............ *G06Q 50/28* (2013.01); *G06Q 10/08* (2013.01); *G06Q 50/22* (2013.01)

(58) Field of Classification Search
None
See application file for complete search history.

(56) References Cited

U.S. PATENT DOCUMENTS

2010/0300041 A1* 12/2010 Kim ............................. 53/281

FOREIGN PATENT DOCUMENTS

| JP | 2005-060085 A | 3/2005 |
|----|---------------|--------|
| JP | 2007-190138 A | 8/2007 |
| JP | 2008-086663 A | 4/2008 |
| KR | 10-2004-0110729 A | 12/2004 |
| KR | 10-2009-0028969 A | 3/2009 |

\* cited by examiner

*Primary Examiner* — Yolanda Cumbess
(74) *Attorney, Agent, or Firm* — Novick, Kimm & Lee, PLLC; Jae Youn Kim (57) ABSTRACT

Disclosed are an automatic medicine warehousing and releasing management system and a method of automatically warehousing and releasing medicines thereof. Warehoused medicines are arranged at proper positions on a storage shelf, and released medicines are discharged from the storage shelf. The automatic medicine warehousing and releasing management system includes a medicine holding and transferring unit to arrange warehoused medicines on a storage rack by holding and accommodating the warehoused medicines according to holding priorities of the medicines based on sizes and expiration dates of the medicines, and release the medicines by holding and accommodating the medicines on the storage rack according to the holding priorities of the medicines, and a medicine warehousing and releasing control unit connected with the medicine holding and transferring unit to control the arranging of medicines requested for warehousing on the storage rack and the discharging of medicines requested for releasing from the storage rack.

8 Claims, 10 Drawing Sheets

AUTOMATIC MEDICINE WAREHOUSING AND RELEASING MANAGEMENT SYSTEM AND METHOD OF AUTOMATICALLY WAREHOUSING AND RELEASING MEDICINES THEREOF

BACKGROUND OF THE INVENTION

1. Field of the Invention

The present invention relates to a technology capable of automatically warehousing and releasing medicines in order to store and manage the medicines. In more detail, the present invention relates to an automatic medicine warehousing and releasing management system capable of arranging warehoused medicines at proper positions on a storage shelf, and discharging released medicines from the storage shelf, and a method of automatically warehousing and releasing medicines thereof.

2. Description of the Related Art

According to a medicine management scheme of the related art, automated facilities to arrange and align medicines are insufficient, so that long time and great manpower are required to re-arrange medicines, which have been already arranged, according to new arrangement conditions.

Although robots, which are able to automatically arrange medicines, have been developed in order to overcome the above problem, the robots carry out only the simple arrangement work based on a medicine storage space, so that an effective alignment arranging work is not performed based on an integrated drug alignment condition.

In addition, since the maximum number of medicines to be stacked and the dimension of a storage space are not calculated based on the dimensions of medicine storage shelves, the space of a medicine storage part is significantly wasted.

In addition, since medicines are not arranged according to the priority of medicine releasing based on a criterion such as the expiration date and the warehoused time of medicines, the release effectiveness of the medicines is not only degraded, but also the stock state of the medicines are not exactly sensed. Accordingly, the effectiveness of the whole medicine management work may be degraded.

SUMMARY OF THE INVENTION

Accordingly, the present invention has been made keeping in mind the above problems occurring in the related art, and an object of the present invention is to provide an automatic medicine warehousing and releasing management system capable of holding and accommodating medicines according to the holding priorities of the medicines, thereby enhancing the efficiency of medicine warehousing and releasing management.

Another object of the present invention is to provide an automatic medicine warehousing and releasing management system further including an identification information recognition unit to manage the names of medicines and the expiration dates of the medicines.

Another object of the present invention is to provide an automatic medicine warehousing and releasing management system further including a medicine size measurement unit to measure the size of the out appearance of a medicine.

Another object of the present invention is to provide an automatic medicine warehousing and releasing management system further including a holding sequence calculation unit to calculate the holding sequence of medicines based on the sizes of the medicines and the expiration dates of the medicines.

Another object of the present invention is to provide an automatic medicine warehousing and releasing management system further including a label generating unit to generate a label having the information of warehoused medicines or released medicines.

Another object of the present invention is to provide an automatic medicine warehousing and releasing management system further including a label attachment unit to attach a label to warehoused or released medicines.

Another object of the present invention is to provide an automatic medicine warehousing and releasing management system further including a warehousing and releasing position search unit to search for a storage rack used to arrange medicines requested for warehousing.

Another object of the present invention is to provide an automatic medicine warehousing and releasing management system further including a medicine holding and transferring unit to transfer a plurality of warehoused or released medicines at once by holding the warehoused or released medicines.

Another object of the present invention is to provide an automatic medicine warehousing and releasing management system further including a holding and transferring control unit to adjust the holding speed of medicines based on the height of the medicines.

Another object of the present invention is to provide a method of automatically warehousing and releasing medicines thereof, capable of calculating the holding sequence of medicines requested for warehousing based on the sizes and the expiration dates of the medicines.

Another object of the present invention is to provide a method of automatically warehousing and releasing medicines thereof, capable of recognizing identification information of warehoused medicines to measure the sizes of the medicines.

Another object of the present invention is to provide a method of automatically warehousing and releasing medicines thereof, capable of calculating the holding sequence of the medicines by assigning a higher priority to a medicine having a smaller size and assigning a higher priority to a medicine having an earlier expiration date.

Another object of the present invention is to provide a method of automatically warehousing and releasing medicines thereof, further including a step of determining the existence of a medicine under deceleration control to adjust the holding speed of the medicine based on the height of the medicine.

Another object of the present invention is to provide a method of automatically warehousing and releasing medicines thereof, capable of automatically arranging medicines, which are introduced into the medicine holding and transferring unit, at proper positions on the storage rack.

Another object of the present invention is to provide a method of automatically warehousing and releasing medicines thereof, capable of arranging medicines in the sequence inverse to the holding sequence of the medicines.

Another object of the present invention is to provide a method of automatically warehousing and releasing medicines thereof, further including a step of effectively re-arranging medicines when the storage rack is cleaned up and the medicines are re-arranged.

Another object of the present invention is to provide a method of automatically warehousing and releasing medicines thereof, capable of maximizing the space of the storage rack when re-arranging the medicines.

Another object of the present invention is to provide a method of automatically managing the releasing of medicines, capable of checking medicines requested for releasing and calculating the holding sequence of the medicines requested for releasing based on the sizes and the expiration dates of the medicines, so that the medicines can be effectively released.

Another object of the present invention is to provide a method of automatically managing the releasing of medicines, capable of generating labels of released medicines and attaching the labels to the medicines.

Another object of the present invention is to provide a method of automatically managing the releasing of medicines, capable of controlling the holding speed of the medicines based on the heights of the medicines when releasing the medicines.

Another object of the present invention is to provide a method of automatically managing the releasing of medicines, further including a step of re-arranging medicines, so that the medicines on the storage rack are re-arranged after medicines have been released.

Another object of the present invention is to provide a method of automatically managing the releasing of medicines, capable of maximizing the utilization of the space of the storage rack by arranging medicines based on the expiration dates of the medicines when re-arranging the medicines.

In order to accomplish the above objects, there is provided an automatic medicine warehousing and releasing management system which includes a medicine holding and transferring unit to arrange warehoused medicines on a storage rack by holding and accommodating the warehoused medicines according to holding priorities of the medicines based on sizes and expiration dates of the medicines, and to release the medicines by holding and accommodating the medicines on the storage rack according to the holding priorities of the medicines, and a medicine warehousing and releasing control unit connected with the medicine holding and transferring unit to control an operation of arranging medicines requested for warehousing on the storage rack and an operation of discharging medicines requested for releasing from the storage rack.

According to the present invention, there is provided a method of automatically warehousing and releasing medicines thereof. The method includes accommodating medicines requested for warehousing by a medicine holding and transferring unit according to a control signal of a medicine warehousing and releasing control unit, arranging the medicines, which are accommodated in the medicine holding and transferring unit, on a storage rack, accommodating the medicines requested for warehousing by using the medicine holding and transferring unit, inputting a list of the medicines requested for warehousing by using a warehousing and releasing list input unit, calculating a medicine holding sequence based on sizes and expiration dates of the medicines requested for warehousing by using a holding sequence calculation unit, and holding the medicines according to the medicine holding sequence and transferring the medicines to the storage rack by using the medicine holding and transferring unit.

According to the present invention, there is provided a method of automatically managing the releasing of medicines. The method includes holding and accommodating medicines requested for releasing by using a medicine holding and transferring unit, and discharging the accommodated medicines to a releasing conveyer by using the medicine holding and transferring unit. The holding and accommodating of medicines requested for releasing includes inputting a list of the medicines requested for releasing by using a warehousing and releasing list input unit, calculating a holding sequence of the medicines requested for releasing by using a holding sequence calculation unit, and transferring the medicines to the releasing conveyer after holding the medicines by using a medicine holding and transferring unit.

As described above, according to the automatic medicine warehousing and releasing management system, medicines are held and accommodated according to the holding priority of the medicines, thereby enhancing the temporal or spatial efficiency according to the medicine warehousing or releasing operation and improving the reliability when managing medicines.

In addition, the identification information recognition unit is additionally provided, so that the information of the names of the medicines and the expiration dates of the medicines can be effectively managed.

In addition, the medicine size measurement unit is additionally provided, so that the size of the outer appearance of each medicine can be measured at various angles.

In addition, the holding sequence calculation unit is additionally provided, so that the holding sequence of the medicines can be systematically calculated based on the information of the sizes and the expiration dates of the medicines.

Further, the label generating unit is additionally provided, so that labels having the information of the warehoused or released medicines can be generated.

In addition, the label attachment unit is additionally provided, so that the labels can be attached to the warehoused or released medicines.

In addition, the warehousing and releasing position search unit is additionally provided, so that the storage rack to arrange the medicines requested for warehousing can be searched for.

Further, the medicine holding and transferring unit is provided to transfer a plurality of warehoused or released medicines at once by holding the warehoused or released medicines.

In addition, the holding and transferring control unit is provided to adjust the holding sequence of the medicines according to the heights of the medicines.

According to the method of automatically warehousing medicines thereof, the medicines requested for warehousing can be effectively arranged on the storage rack by calculating the holding sequence based on the size and the expiration dates of the medicines.

In addition, the identification information of the warehoused medicines can be recognized and the size of the medicines can be exactly measured.

In addition, the higher priority is assigned to the medicine having the smaller size, and assigned to a medicine having an earlier expiration date, thereby calculating the proper holding sequence of medicines as the medicines are warehoused.

In addition, the step of determining the existence of the medicine under deceleration control is additionally provided, thereby adjusting the holding speed of the medicine based on the height of the medicine.

In addition, the medicine introduced into the medicine holding and transferring unit can be automatically arranged at the proper position on the storage rack.

In addition, the medicines can be arranged in the sequence inverse to the holding sequence of the medicines.

In addition, the step of re-arranging the medicines is additionally provided, thereby effectively re-arranging the medicines when cleaning up the storage rack and re-arranging the medicines.

In addition, when the medicines are re-arranged, the use of the space in storage rack can be maximized.

According to the method of automatically managing the releasing of the medicines, the medicines requested for releasing is checked, and the holding sequence of the medicines is calculated based on the sizes and the expiration dates of the medicines, thereby effectively releasing the medicines.

In addition, the label of the released medicines can be generated and attached.

In addition, when the medicines are released, the holding speeds of the medicines can be adjusted based on the heights of the medicines.

In addition, the step of re-arranging medicines is additionally provided, thereby re-arranging the medicines on the storage rack after medicines have been released.

Further, when the medicines are re-arranged, the medicines can arranged based on the expiration dates thereof, and the use of the space in storage rack can be maximized.

DETAILED DESCRIPTION OF THE INVENTION

Hereinafter, the automatic medicine warehousing and releasing management system according to the embodiment the present invention will be described in detail.

Figure 1:
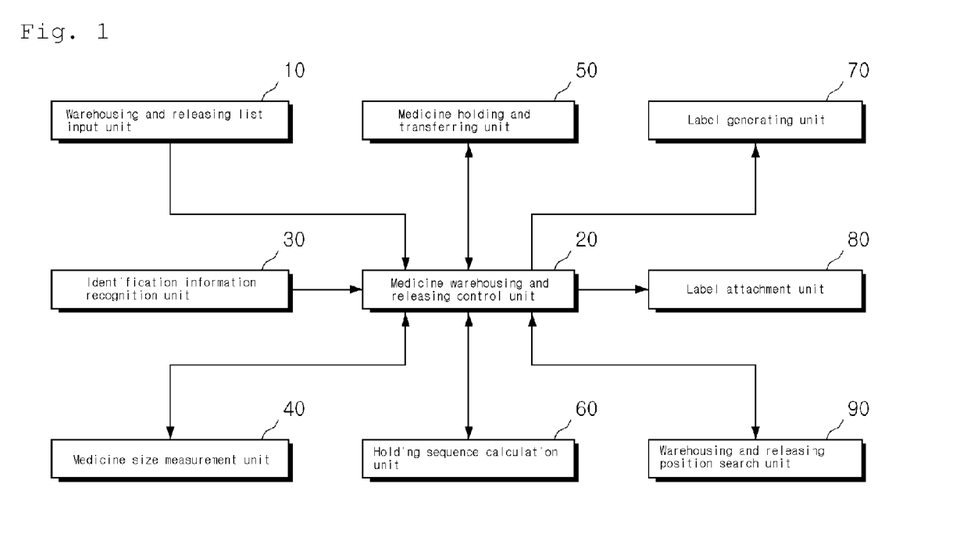
FIG. 1 is a block diagram showing the structure of an automatic medicine warehousing and releasing management system according to the present invention.

FIG. 1 is a block diagram showing the structure of an automatic medicine warehousing and releasing management system according to the present invention. The automatic medicine warehousing and releasing management system includes a warehousing and releasing list input unit 10, a medicine warehousing and releasing control unit 20, an identification information recognition unit 30, a medicine size measurement unit 40, a medicine holding and transferring unit 50, a holding sequence calculation unit 60, a label generating unit 70, a label attachment unit 80, and a warehousing and releasing position search unit 90.

The warehousing and releasing list input unit 10 inputs the list of medicines requested for warehousing or releasing therein. The list of the medicines input by the warehousing and releasing list input unit 10 is transferred to the medicine warehousing and releasing control unit 20.

The medicine warehousing and releasing control unit 20 controls an operation of arranging the medicines, which are requested for warehousing, on a storage rack, and an operation of releasing medicines, which are requested for releasing, from the storage rack based on the list of medicines received therein from the warehousing and releasing list input unit 10.

The identification information recognition unit 30 recognizes the identification information of the medicines, and the identification information recognized by the identification information recognition unit 30 is transferred to the medicine warehousing and releasing control unit 20.

In addition, the identification information according to the present invention includes information used to manage the information of the name of medicines, and the expiration date of the medicines. According to the embodiment of the present invention, the identification information of the medicines is recognized by using a barcode including the basic information of the medicines.

The medicine size measurement unit 40 is connected with the medicine warehousing and releasing control unit 20 to measure the size of the outer appearance of the medicines. The medicines according to the embodiment of the present invention have a hexagonal shape. The size of the outer appearance of the medicines is calculated by measuring the length and the width of a base side of each medicine and the height of the medicine.

The medicine holding and transferring unit 50 is connected with the medicine warehousing and releasing control unit 20 to hold and accommodate warehoused medicines according to the holding priority based on the sizes and the expiration dates of the medicines and arrange the medicines on the storage rack. In addition, the medicine holding and transferring unit 50 holds and accommodates the medicines, which are arranged on the storage rack, therein according to the holding priority and releases the medicines from the storage rack.

Figure 2:
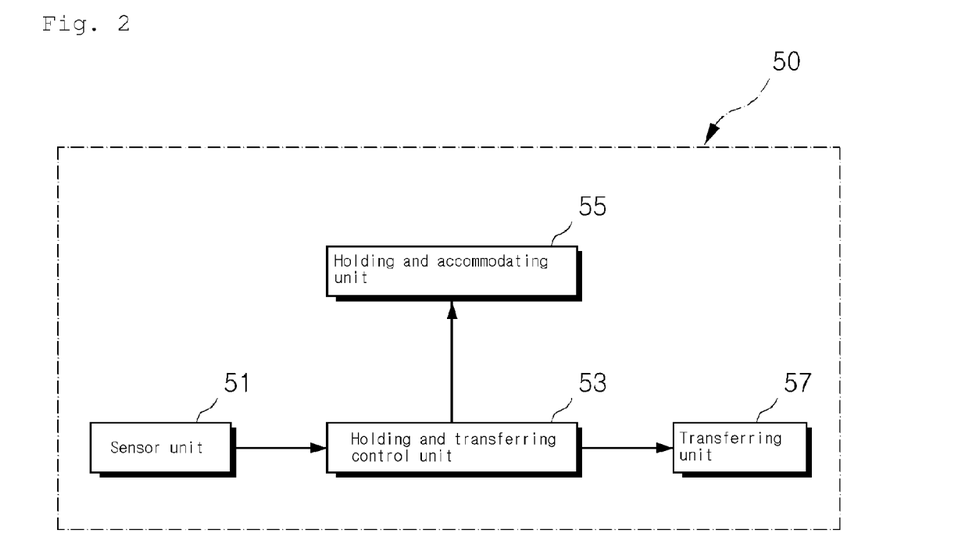
FIG. 2 is a detailed block diagram showing the structure of a medicine holding and transferring unit of an automatic medicine warehousing and releasing management system according to the present invention.

In addition, as shown in FIG. 2, the medicine holding and transferring unit 50 according to the present invention includes a sensor unit 41, a holding and transferring control unit 53, a holding and accommodating unit 55, and a transferring unit 57.

The sensor unit 41 senses the medicines transferred to a medicine warehousing container or a medicine releasing container, and sends the sensed signal to the holding and transferring control unit 53.

The holding and transferring control unit 53 controls an operation of holding and transferring the medicine sensed by the sensor unit 41.

The holding and accommodating unit 55 is connected with the holding and transferring control unit 53 to hold and accommodate the medicine sensed by the sensor unit 51. Then, the holding and accommodating unit 55 discharges the accommodated medicine to the outside.

The transferring unit 57 is connected with the holding and transferring control unit 53 to transfer the holding and accommodating unit 55 to the storage rack to store medicines, or transfer the holding and accommodating unit 55 to the medicine warehousing container or the medicine releasing container.

The holding sequence calculation unit 60 is connected with the medicine warehousing and releasing control unit 20 to calculate the sequence of medicines held by the medicine holding and transferring unit 50 based on the information of the sizes and the expiration dates of the medicines.

The holding sequence of the medicines according to the present invention is made by assigning a higher priority to a medicine having a smaller size. When medicines have the same size, a higher priority is assigned to a medicine having an earlier expiration date.

The label generating unit 70 is connected with the medicine warehousing and releasing control unit 20 to generate a label having warehousing or releasing information of warehoused or released medicines.

In other words, the label including information of a warehousing date, a warehousing time, a releasing date, a releasing time, and a manager to request warehousing or releasing a medicine is generated, so that the check of the releasing or warehousing information of the medicines can be easily performed.

The label attachment unit 80 is connected with the medicine warehousing and releasing control unit 20 to attach the label generated by the label generating unit 70 to the medicines.

Preferably, the label attachment unit 80 according to the present invention identically sets label attachment surfaces among outer surfaces of the medicines.

The warehousing and releasing position search unit 90 is connected with the medicine warehousing and releasing control unit 20 to search for the proper position of the storage rack for the arranging of the medicines requested for warehousing, or to search for a storage rack having medicines requested for releasing.

In addition, the warehousing and releasing position search unit 90 searches for the information of medicines stored in the storage rack, searches for a storage rack in which warehoused medicines may be arranged, and searches for the storage position of the medicines requested for releasing, thereby enhancing the efficiency when warehousing or releasing medicines.

As described above, when the automatic medicine warehousing and releasing management system according to the present invention is employed, medicines are held and accommodated according to the holding priorities of the medicines, thereby enhancing the temporal or spatial efficiency according to the medicine warehousing or releasing operation and improving the reliability when managing medicines.

Hereinafter, a method of automatically warehousing and releasing medicines by using the automatic medicine warehousing and releasing management system according to the present invention will be described.

Figure 3:
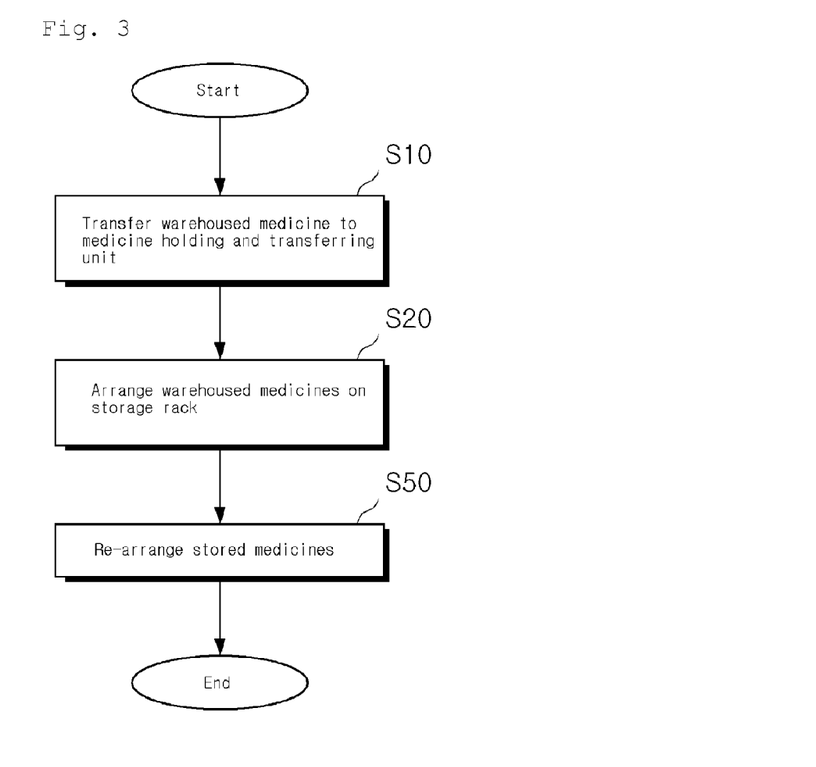
FIG. 3 is a flowchart showing a method of automatically warehousing and releasing medicines according to the present invention.

FIG. 3 is a flowchart showing the whole procedure of a method of automatically warehousing and releasing medicines according to the present invention. In this case, the medicines requested for warehousing are accommodated in the medicine holding and transferring unit 50 (step S10).

Figure 4:
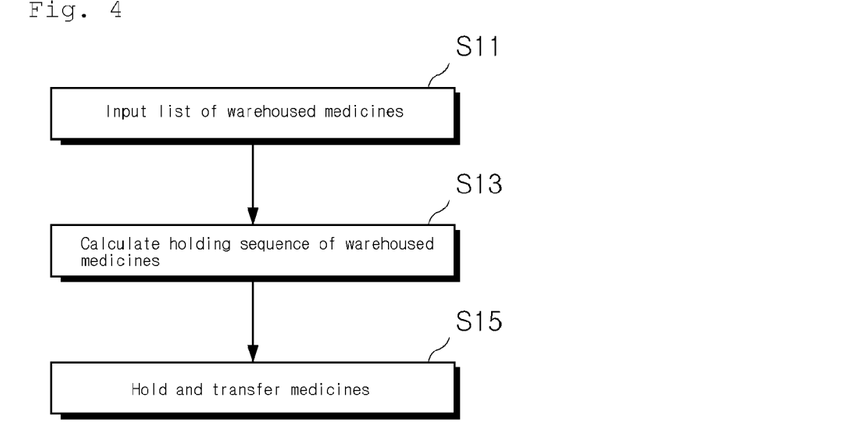
FIG. 4 is a detailed flowchart showing step S10 in the method of automatically warehousing and releasing the medicines according to the present invention.

FIG. 4 is a detailed flowchart showing step S10 according to the present invention. In this case, a step of input the list of medicines requested for warehousing is performed by using the warehousing and releasing list input unit 10 (step S11).

In step S11, the list of medicines may include the names of medicines, a pharmaceutical company, and the number of warehoused medicines.

Next, a step of calculating the holding sequence of the medicines based on the sizes of the medicines requested for warehousing and the expiration dates of the medicines is performed by using the holding sequence calculation unit 60 (step S13).

Figure 5:
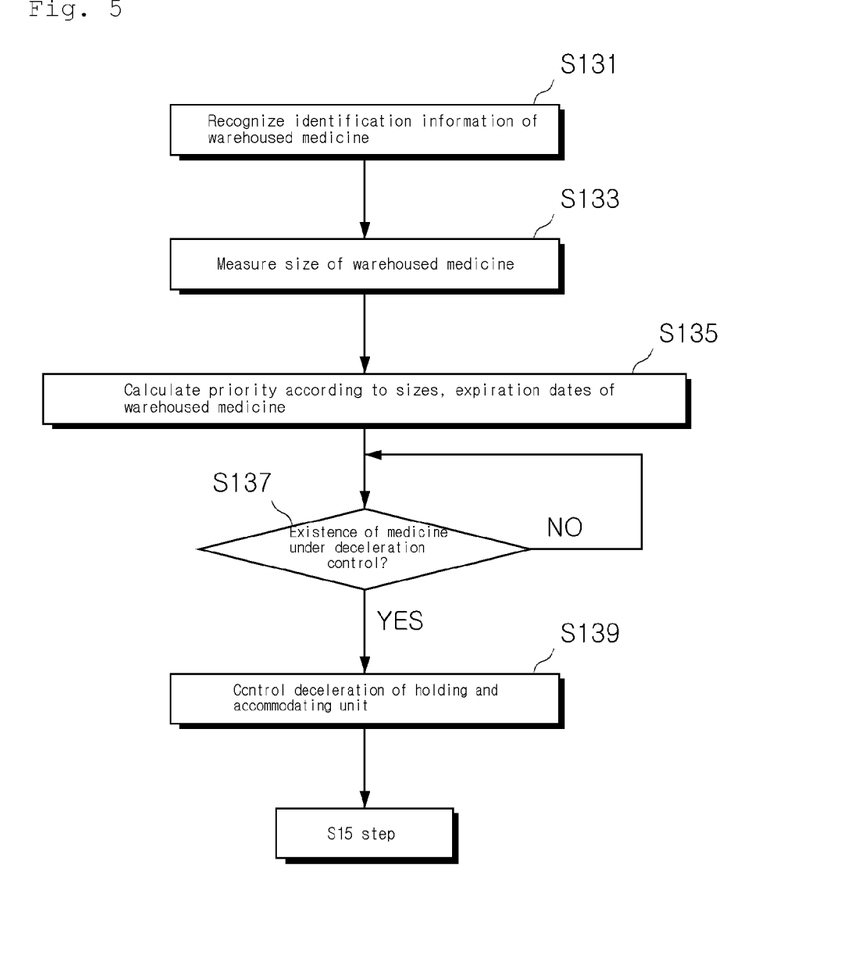
FIG. 5 is a detailed flowchart showing step S13 in the method of automatically warehousing and releasing the medicines according to the present invention.

FIG. 5 is a detailed flowchart showing step S13. A step of recognizing the identification information of the medicines requested for warehousing is performed by using the identification information recognition unit 30 (step S131).

Although the identification information in step S131 includes barcode information according to the embodiment of the present invention, the present invention is not limited. In other words, the identification information can be recognized by using various identification members.

A step of measuring the sizes of the medicines requested for warehousing is performed by using the medicine size measurement unit 40 (step S133).

In step S133, the width and length of the base side of each medicine and the height of the medicine are preferably measured.

Thereafter, a step of calculating the priority based on the sizes and the expiration dates of the medicines is performed (step S135).

In step S135 according to the present invention, a higher priority is assigned to a medicine having a smaller size. When medicines have the same size, a higher priority is assigned to a medicine having an earlier expiration date.

Next, a step of determining if medicines under deceleration control exist is performed (step S137).

In step S137 according to the present invention, the medicine under the deceleration control is determined based on a height reference value N according to the area of the medicine. The reference value N may be set according to the area of the medicine and the speed of the holding and accommodating unit, compared with a value obtained by dividing the square of the height of the medicine by the area of the medicine for the purpose of determination, and expressed as Equation 1.

$$\frac{Height^2}{Width \times Length} > N \qquad \text{Equation 1}$$

If a medicine having a measurement value higher than the reference value N is sensed, the step of decelerating the speed of the holding and accommodating unit 55 is preferably performed.

Next, a step of holding a medicine according to the holding sequence of the medicines and transferring the medicine to the storage rack is performed by using the medicine holding and transferring unit 50 (step S15).

In step S15, when a plurality of medicines having the same width exist, the plural medicines may be held and transferred at once.

Figure 6:
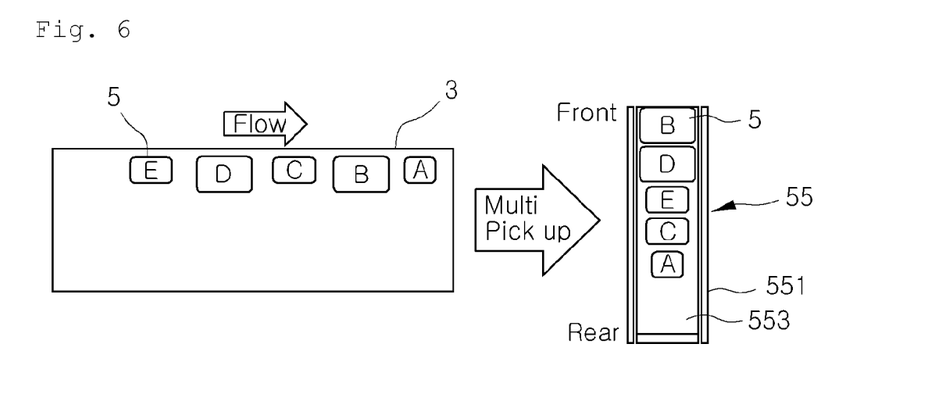
FIG. 6 is a schematic view showing step S10 in the method of automatically warehousing and releasing the medicines according to the present invention.

FIG. 6 is a schematic view showing step S10 according to the present invention. In step S10, a plurality of A, B, C, D, and E medicines 5 requested for warehousing are introduced into the warehousing container 3, and the medicines 5 are held by using the medicine holding and transferring unit 50.

In this case, a higher priority is assigned to a medicine having a smaller width (A<C, E<B, D). When the medicines C and E have the same width, a higher priority is assigned to a medicine having an earlier expiration date (medicine C). In the case of the medicines B and D, a higher priority is assigned to the medicine D having an earlier expiration date.

The holding and accommodating unit 55 of the medicine holding and transferring unit 50 includes an arm 551 to hold a medicine by pressurizing both sides of the medicine and an accommodation unit 553 to accommodate the medicine held by the arm 551. If the medicines are held in the sequence in which the warehoused medicines are held, the medicines may be held in the sequence of medicines A, C, E, D, and B.

The medicines accommodated by the medicine holding and transferring unit 50 are arranged on the storage rack (step S20).

Figure 7:
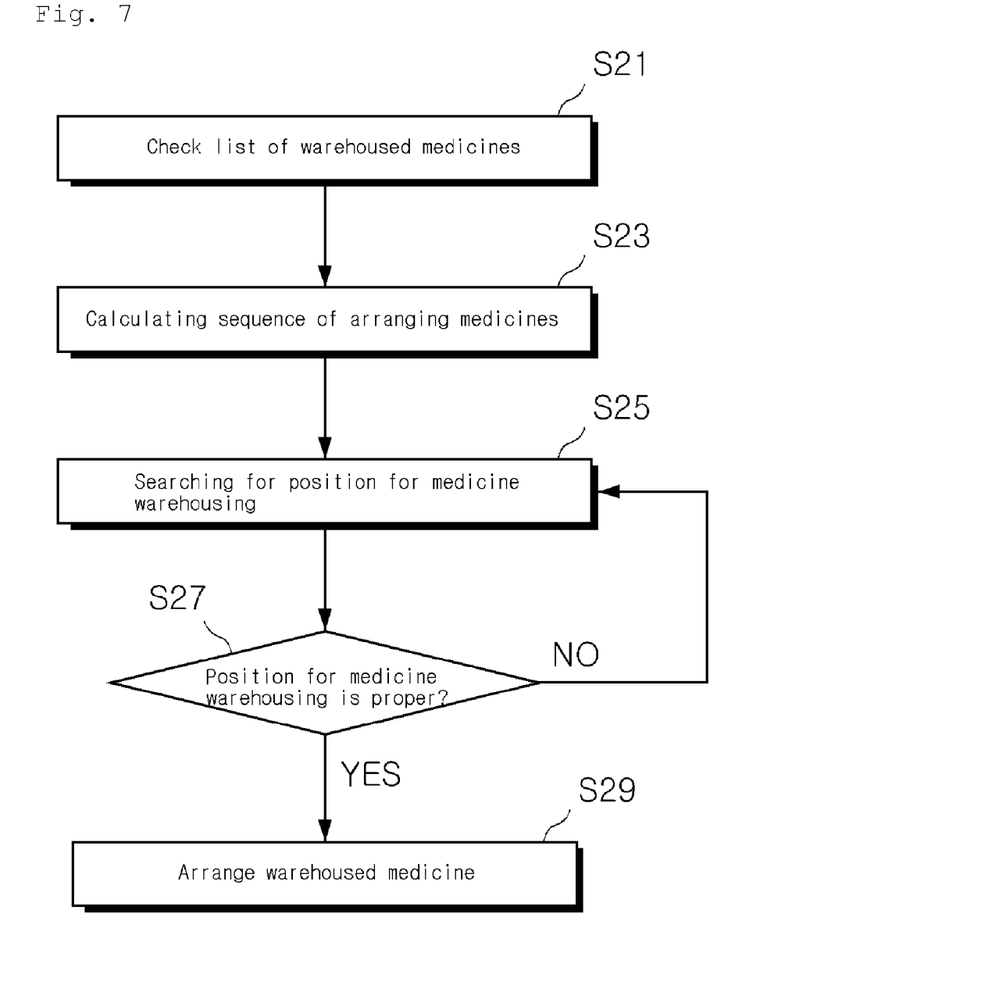
FIG. 7 is a flowchart showing step S20 in the method of automatically warehousing and releasing the medicines according to the present invention.

FIG. 7 is a detailed flowchart showing step S20. A step of checking the list of warehoused medicines accommodated by the medicine holding and transferring unit 50 is performed (step S21).

Thereafter, a step of calculating the sequence of arranging medicines is performed by using the holding sequence calculation unit 60 (step S23).

In step S23, the sequence of arranging the medicines is calculated as the inverse sequence to the holding sequence of the medicines in step S13.

Next, a step of searching for the proper position on the storage rack suitable for arranging the medicine is performed by using the warehousing and releasing position search unit 90 (step S25).

Preferably, in step S25, the proper position is searched for by taking into consideration the positions of the same kinds of medicines, which have been previously stored, and the expiration dates of the medicines.

Step S27 of determining if the position of the storage rack is proper when the medicines are warehoused is performed. If the position of the storage rack is proper, the medicine is transferred to the searched storage rack and arranged on the searched storage rack (step S29).

Preferably, if the searched storage rack is not a proper position in step S27, step S25 is returned and the operation from step S25 is re-performed.

Figure 8:
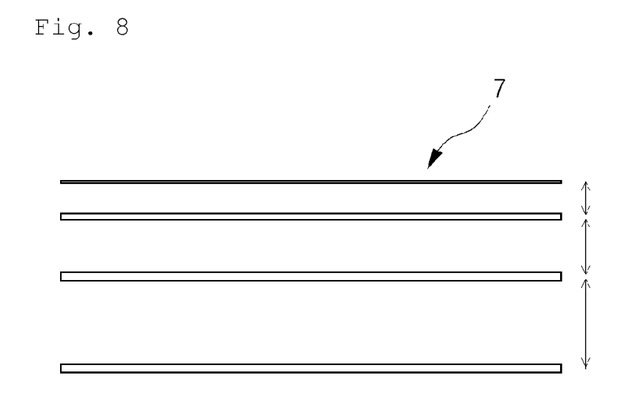
FIG. 8 is a view showing the height of a storage rack for medicine warehousing in the method of automatically warehousing and releasing the medicines according to one embodiment of the present invention.
Figure 9:
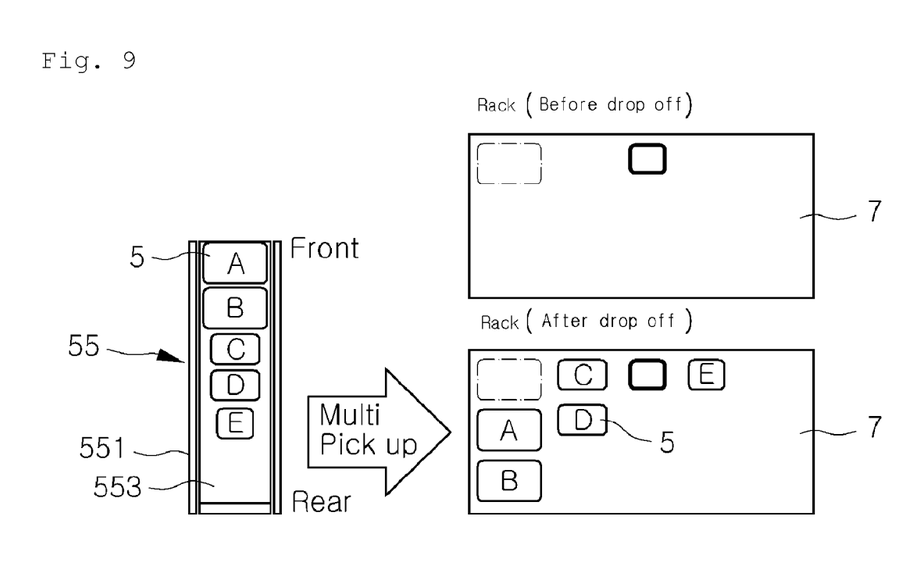
FIG. 9 is a schematic view showing step S20 in the method of automatically warehousing and releasing the medicines according to one embodiment the present invention.

FIG. 3 is a view showing the height of the medicine storage rack according to the present invention. If the height of the A medicine is 25, the medicine A is preferably arranged on storage rack #2. If the height of the medicine B is 35, the medicine A is preferably arranged on storage rack #3.

As described above, according to the method of automatically warehousing and releasing the medicines of the present invention, a medicine is arranged on a storage rack by taking the width and the length of a base side of the medicine and the height of the medicine into consideration. Accordingly, the use of the space in storage rack can be maximized.

In addition, the method of automatically warehousing and releasing the medicines according to the present invention preferably further includes a step of re-arranging the stored medicines (step S50) after step S20.

Figure 16:
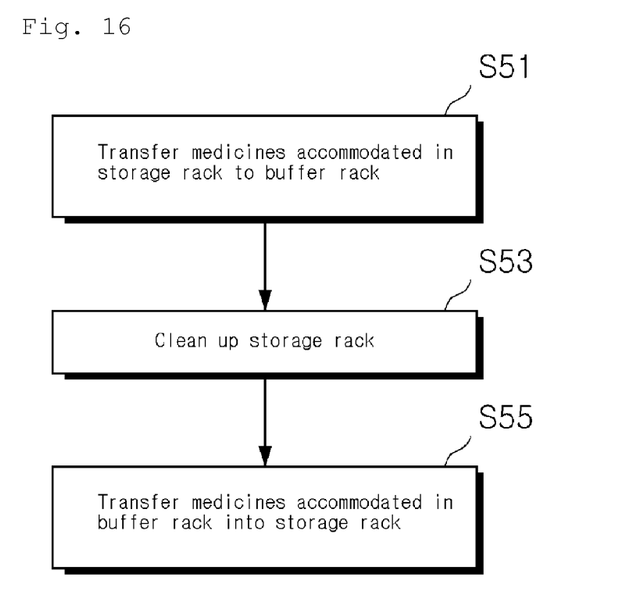
FIG. 16 is a detailed flowchart showing step S50 in the method of automatically releasing medicines.

FIG. 16 is a detailed flowchart showing step S50 according to the present invention. Step S51 of transferring medicines arranged on the storage rack to a buffer rack is performed by using the medicine holding and transferring unit 50, and then a step of cleaning up the inner part of the storage rack is performed (step S53).

Thereafter, the medicines accommodated in the buffer rack are transferred into the storage rack 7 and arranged on the storage rack 7 (step S55).

Figure 17:
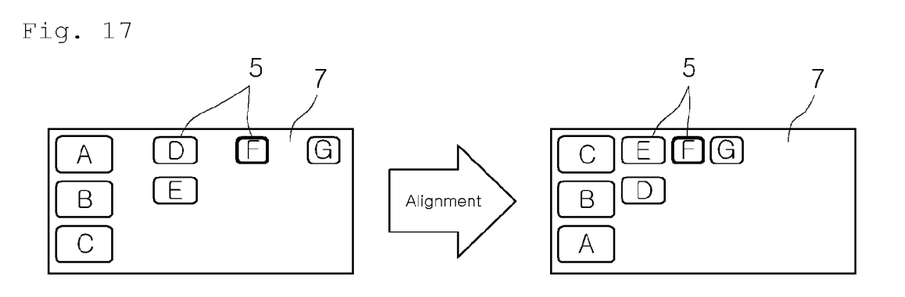
FIG. 17 is a schematic view showing step S50 in the method of automatically releasing medicines.

FIG. 17 is a view showing step S50 according to one embodiment of the present invention. When the medicines stored in the storage rack 7 are re-arranged, preferably, a medicine having an earlier expiration date is first held based on the expiration dates, and medicines are arranged on the storage rack 7 in the sequence inverse to the holding sequence of the medicines.

In addition, preferably, medicines are arranged as densely as possible so that the remaining space does not make in the storage rack 7.

Hereinafter, a method of automatically warehousing and releasing medicines by using the automatic medicine warehousing and releasing management system according to the present invention will be described.

Figure 10:
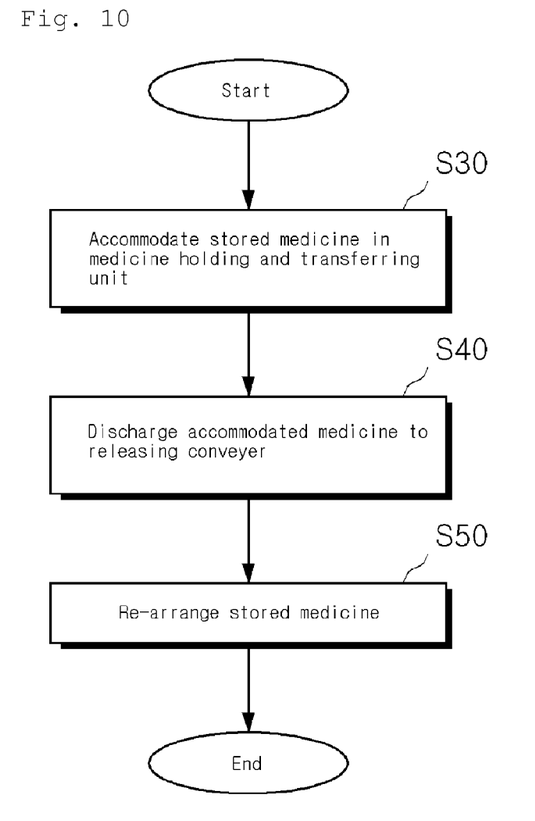
FIG. 10 is a flowchart showing a method of automatically releasing medicines according to the present invention.

FIG. 10 is a flowchart showing the whole procedure of the method of automatically releasing medicines. A step of holding and accommodating the medicines requested for releasing is performed by using the medicine holding and transferring unit 50 (step S30).

Figure 11:
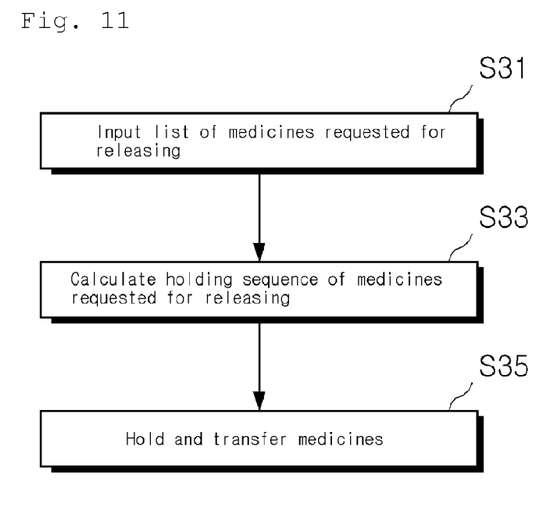
FIG. 11 is a flow chart showing step S30 in the method of automatically releasing the medicines.

FIG. 11 is a detailed flowchart showing step S30. A step of inputting the list of medicines requested for releasing is performed by using the warehousing and releasing list input unit 10 (step S31).

In step S31, the list of medicines requested for releasing includes information of the name of medicines requested for releasing, a pharmaceutical company, and the number of medicines.

Next, a step of calculating the holding sequence of the medicines requested for releasing is performed by using the holding sequence calculation unit 60 (step S33).

Figure 12:
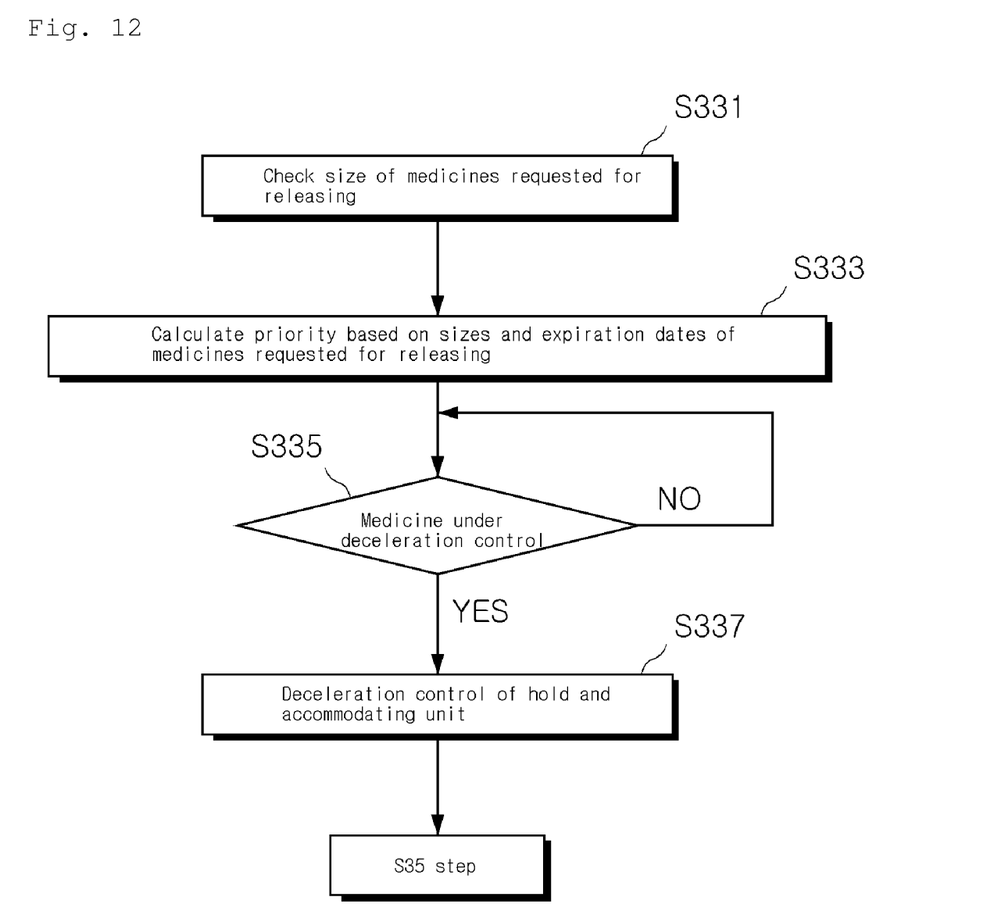
FIG. 12 is a flowchart showing step S33 in the method of automatically releasing the medicines.

FIG. 12 is a detailed flowchart step S33. A step of checking the sizes of the medicines requested for releasing is performed by using the medicine warehousing and releasing control unit (step S331).

A step of calculating the holding sequence of medicines based on the sizes slug the expiration dates of the medicines requested for releasing is performed (step S333).

The holding sequence of the medicines according to the present invention is made by assigning a higher priority to a medicine having a smaller size. When medicines have the same size, a higher priority is assigned to a medicine having an earlier expiration date.

Next, a step of determining if medicines under deceleration control exist is performed by using the holding and transferring control unit 53 (step S335).

The medicine under deceleration control according to the present invention is determined based on the reference value N according to the area of the medicine. The reference value N according to the area of the medicine is calculated based on a value obtained by dividing the square of the height of the medicine by the area of the medicine. The reference equation to sense the deceleration control can be expressed as Equation 1.

If a medicine representing a measurement value higher than the reference value K is sensed in step S335, a step of decelerating the speed of the holding and accommodating unit 55 is preferably performed.

Next, a step of holding medicines according to the holding sequence of medicines and transferring the medicines to the releasing conveyer is performed by using the medicine holding and transferring unit 50 (step S35).

Figure 13:
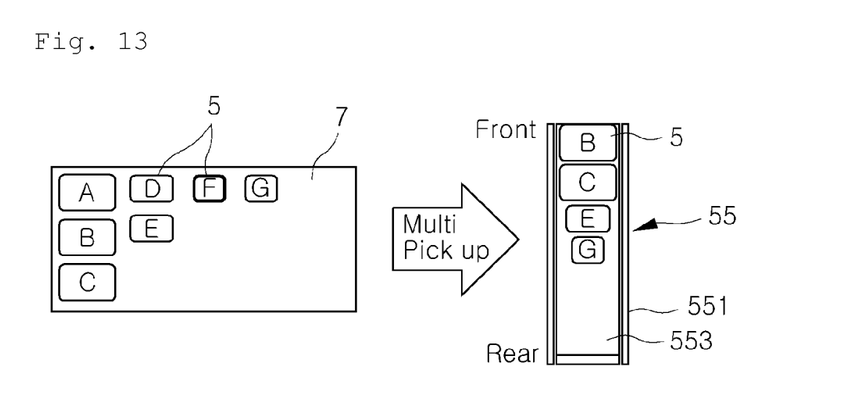
FIG. 13 is a schematic view showing step S30 in the method of automatically releasing the medicines according to the present invention.

FIG. 13 is a flowchart showing step S30 according to one embodiment. If the holding sequence of medicines is determined based on the sizes and the expiration dates of the medicines with respect to medicines stored in the storage rack 7, the medicine 5 is held by using the medicine holding and transferring unit 50.

In this case, a higher priority is assigned to a medicine having a smaller width (G<F<D, E<A, B, C). When the medicines A, B, and C have the same size, a higher priority is assigned to a medicine having an earlier expiration date (A<B<C). In the case of medicines D and E, a higher priority is assigned to the medicine D having an earlier expiration date.

The holding and accommodating unit 55 of the medicine holding and transferring unit 50 includes the arm 551 to hold a medicine by pressurizing both sides of the medicine and the accommodation unit 553 to accommodate the medicine held by the arm 551. If the medicines are held in the sequence in which the warehoused medicines are held, the medicines may be held in the sequence of medicines G, E, C, and B. When the medicines B and C having the same width are stored in a line, the medicines B and C are held at once.

Similarly to another embodiment shown in FIG. 17, the arm 551 according to the present invention preferably further includes inclined pads 555 provided at both end portions of internal lateral sides facing each other.

The pad 555 prevents the held medicine from deviating from the arm 551. In general, medicines are different from each other with the same width, or are placed at different positions. In this case, the arm 551 must sequentially hold the medicines. However, since the holding width of the arm 551 is fixed due to the width of the medicine, which has already held, the same medicines may not be sequentially held.

In this case, when the pad 555 according to the present invention is formed, different medicines having the same width may be easily held.

Figure 14:
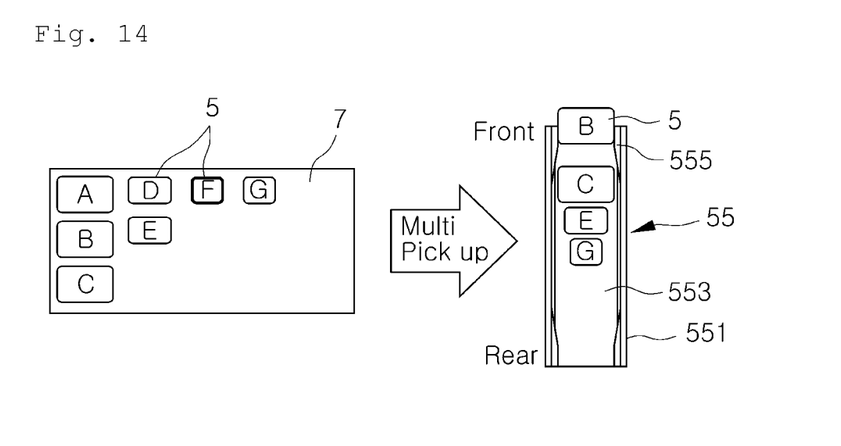
FIG. 14 is a schematic view showing step S30 in the method of automatically releasing medicines according to another embodiment.

According to the embodiment of the present invention, when medicines A, B, C, D, E, F, and G are stored, a higher priority is assigned to a medicine having a smaller width (G<F<D, E<A, B, C). When medicines A, B, and C have the same width, a higher priority is assigned to a medicine having an earlier expiration date (A<B<C). In the case of medicines D and E, a higher priority is assigned to the medicine D having an earlier expiration date.

In addition, the medicines G, E, C, and B to be released are sequentially held through one side of the arm 551 having the pad 55.

In this case, since the width of the arm 551 is fixed to the width of the pad 555, the medicines C and B are sequentially held.

Next, the accommodated medicines accommodated are discharged through the released conveyer by using the medicine holding and transferring unit 50 (step S40).

Figure 15:
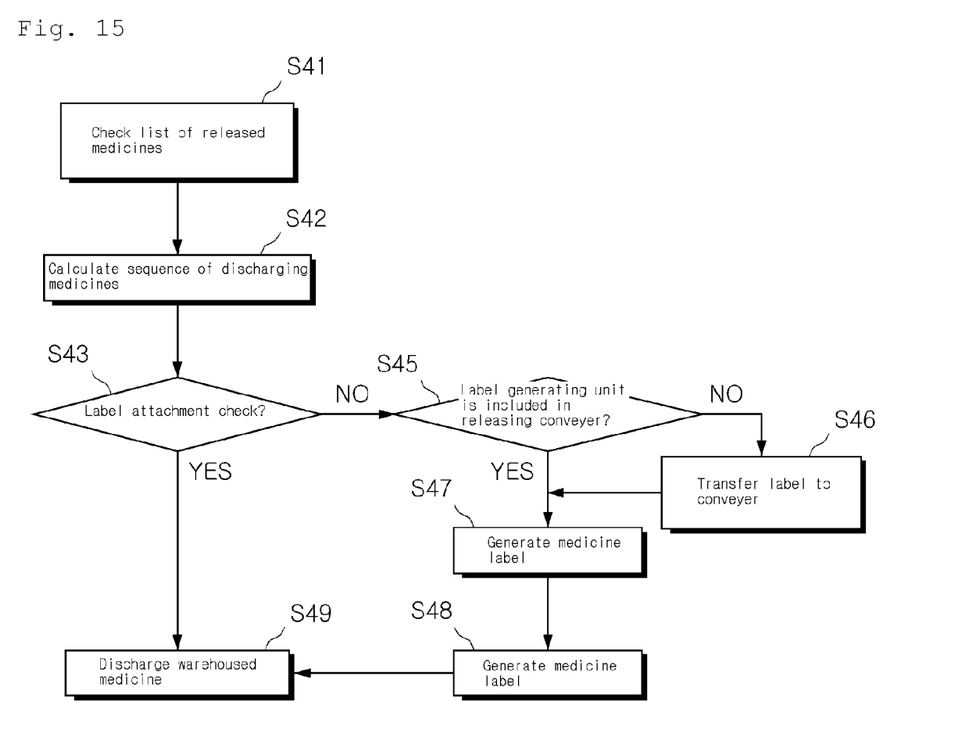
FIG. 15 is a flowchart showing step S40 in the method of automatically releasing medicines.

FIG. 15 is a detailed flowchart showing step S40. In this case, a step of checking a list of released drugs accommodated in the medicine holding and transferring unit 50 is performed (step S41).

Next, a step of calculating the sequence of discharging medicines accommodated in the medicine holding and transferring unit 50 is performed (step S42).

In step S42, the sequence of discharging the medicines is calculated as the sequence inverse to the holding sequence of the medicines in step S333.

Thereafter, a step of checking the attachment state of a label of the released medicines is performed by using the identification information recognition unit 30.

When the label is attached to the medicine in step S43, a step of discharging the medicines to the released conveyer 3 is performed (step S44).

When the label is not attached to the medicine in step S43, a step of determining if a label generating unit is included in the released conveyer is performed (step S45).

If the label generating unit 70 is integrated with the released conveyer 3 in step S45, a label including the information of medicine releasing is generated by using label generating unit 70 (step S46), and the label is attached to the surface of the medicine by using label attachment unit 80 (step S47). Accordingly, a step of discharging the medicine to the releasing conveyer is performed (step S49).

If the label generating unit 70 is not integrated with the released conveyer 3 in step S45, the transfer to the label conveyer including an additional label generating unit 70 is performed (step S46), so that steps S47 to S49 are performed.

Preferably, according to the method of automatically releasing the medicines, the step of re-arranging medicines arranged on the storage rack is performed after step S40. Step S50 is the same as the step described in the method of automatically warehousing and releasing the medicines according to the present invention.

As described above, when the method of automatically managing the releasing of medicines according to the present invention is applied, the medicines requested for releasing is checked, and the holding sequence is calculated based on the sizes and the expiration dates of the medicines, so that medicines can be effectively released. The label including the releasing information of the released medicines is attached, so that the releasing information of the medicines can be systematically managed.

Although a preferred embodiment of the present invention has been described for illustrative purposes, those skilled in the art will appreciate that various modifications, additions and substitutions are possible, without departing from the scope and spirit of the invention as disclosed in the accompanying claims.

What is claimed is:

1. An automatic medicine warehousing and releasing management system comprising:
    a medicine holding and transferring unit to arrange warehoused medicines on a storage rack by holding and accommodating the warehoused medicines according to holding priorities, wherein the holding priorities are determined by both the sizes of the medicines and the expiration dates of the medicines, and to release the medicines on the storage rack according to the holding priorities of the medicines;
    a medicine warehousing and releasing control unit connected to the medicine holding and transferring unit to control an operation of arranging medicines requested for warehousing on the storage rack and an operation of discharging medicines requested for releasing from the storage rack; and
    a holding sequence calculation unit connected to the medicine warehousing and releasing control unit to calculate a holding sequence of the medicines held by the medicine holding and transferring unit based on the information of the sizes and the expiration dates of the medicines, wherein a higher priority is assigned to a medicine having a smaller size, and assigned to a medicine having an earlier expiration date when the holding sequence of the medicines is calculated.

2. The automatic medicine warehousing and releasing management system of claim 1, further comprising an identification information recognition unit connected to the medicine warehousing and releasing control unit to recognize identification information of the medicines, wherein the identification information comprises information used to manage information of a name of each medicine and an expiration date of the medicine.

3. The automatic medicine warehousing and releasing management system of claim 1, further comprising a medicine size measurement unit connected to the medicine warehousing and releasing control unit to measure a size of an outer appearance of the medicine.

4. The automatic medicine warehousing and releasing management system of claim 1, further comprising a warehousing and releasing list input unit connected to the medicine warehousing and releasing control unit to input a list of the medicines requested for warehousing or releasing.

5. The automatic medicine warehousing and releasing management system of claim 1, further comprising:
    a label generating unit connected to the medicine warehousing and releasing control unit to generate a label having warehousing or releasing information of the warehoused or released medicines; and
    a label attachment unit to attach the label generated from the label generating unit to the warehoused or released medicines.

6. The automatic medicine warehousing and releasing management system of claim 1, further comprising a warehousing and releasing position search unit connected to the medicine warehousing and releasing control unit to search for a proper position of the storage rack for arranging of the medicines requested for warehousing, or to search for a storage rack having the medicines requested for releasing which is arranged therein.

7. The automatic medicine warehousing and releasing management system of claim 1, wherein the medicine holding and transferring unit comprises:
    a sensor unit to sense a medicine transferred to a medicine warehousing container or a medicine releasing container;
    a holding and transferring control unit connected to the sensor unit to control an operation of holding and transferring the medicine sensed by the sensor unit;
    a holding and accommodating unit connected to the holding and transferring control unit to hold and accommodate the medicine sensed by the sensor unit and to discharge the accommodated medicine to an outside; and
    a transferring unit connected to the holding and transferring control unit to transfer the medicine held by the holding and accommodating unit to the storage rack.

8. The automatic medicine warehousing and releasing management system of claim 7, wherein the holding and transferring control unit compares a height reference value (N) according to an area of the medicine to control a driving speed of the holding and accommodating unit, the height reference value (N) according to the area of the medicine is calculated based on a value obtained by dividing a square of a height of the medicine by the area of the medicine, and, if a medicine having a measurement value higher than the height reference value (N) is sensed, the driving speed of the holding and accommodating unit is reduced.

* * * * *